United States Patent
He et al.

(10) Patent No.: US 6,815,450 B2
(45) Date of Patent: Nov. 9, 2004

(54) AXON REGENERATION WITH PKC INHIBITORS

(75) Inventors: Zhigang He, Boston, MA (US); Vuk Koprivica, Boston, MA (US); Rajeev Sivasankaran, Boston, MA (US)

(73) Assignee: Children's Medical Center Corporation, Boston, MA (US)

( * ) Notice: Subject to any disclaimer, the term of this patent is extended or adjusted under 35 U.S.C. 154(b) by 0 days.

(21) Appl. No.: 10/389,082

(22) Filed: Mar. 14, 2003

(65) Prior Publication Data

US 2003/0176424 A1 Sep. 18, 2003

Related U.S. Application Data

(63) Continuation of application No. 10/100,690, filed on Mar. 14, 2002, now Pat. No. 6,664,266.

(51) Int. Cl.⁷ .............................................. A61K 31/44
(52) U.S. Cl. .................. 514/294; 514/252.12; 514/552; 514/547; 514/253.05
(58) Field of Search ............................. 514/294, 252.12, 514/253.05, 552, 547

(56) References Cited

U.S. PATENT DOCUMENTS

| 5,385,915 A | 1/1995 | Buxbaum et al. |
| 5,461,146 A | 10/1995 | Lewis et al. |
| 6,268,352 B1 | 7/2001 | Song et al. |

OTHER PUBLICATIONS

Prang et al. 2001, Experimental Neurology, 169:135–47.

*Primary Examiner*—Marianne C. Seidel
*Assistant Examiner*—C. Delacroix-Muirheid
(74) *Attorney, Agent, or Firm*—Richard Aron Osman

(57) ABSTRACT

Regenerative growth of an adult mammalian central nervous system neuron axon subject to growth inhibition by endogenous, myelin growth repulsion factors is promoted by delivering to the axon a therapeutically effective amount of a specific inhibitor of protein kinase C, whereby regenerative growth of the axon is promoted and a resultant promotion of the regenerative growth of the axon is detected.

21 Claims, No Drawings

AXON REGENERATION WITH PKC INHIBITORS

CROSS-REFERENCE TO RELATED APPLICATION

This application is a continuation under 35 U.S.C.§120 to U.S. Ser. No. 10,100,690, filed Mar. 14, 2002, now U.S. Pat. No. 6,664,266, having the same title and inventors, which is incorporated herein by reference.

This work was supported by Federal Grant No. 1R21NS41999-01 from NINDS and No. 1R01NS42252 from NIDA. The government may have rights in any patent issuing on this application.

INTRODUCTION

1. Field of the Invention

The invention is in the field of promoting axon regeneration with PKC inhibitors.

2. Background of the Invention

Protein kinase C (PKC) is ubiquitously expressed in CNS tissues. Behavioral, genetic and pharmacological evidence have associated PKC activity with a wide range of neural functions, from controlling neurotransmitter release and synaptic efficacy to learning and memory processes (Tanaka et al., Annu Rev Neurosci 1994, 17, 551–67; Le Merrer et al., Pharmacol Res 2000, 41, 503–14; Battaini, 2001, Pharmacol Res 44, 1043–61). In addition, PKC activation has been implicated in neural cell proliferation, contraction and survival (Maher 2001, J Neurosci 21, 2929–38). For examples, PKC inhibitors have been reported to block neurite outgrowth in retinal axons (Heacock et al. 1997 Neurochem Res 22, 1179–850), dorsal root ganglion neurons (Theodore et al. 1995, J Neurosci 15, 7185–97), sympathetic neurons (Campenot et al. 1994, J. Neurochem 63, 868–78), PC12 cells (Kolkova et al. 2000 J Neurosci 20, 2238–46) and hippocampal organotypic cultures (Toni et al. Synapse 27, 199–207) PKC inhibitors have also been shown to promote dendritic growth in Purkinje cells in cerebellar slice cultures (Metzger et al. 2000, Eu J Neurosci 12, 1993–2005) and to promote extension of dorsal root ganglion cells filopodia (Bonsall et al. 1999, Brain Res 839, 120–32); see also, Prang et al. 2001, Exp Neuro 169, 135–147; Powell et al. 2001, Glia 33, 268–97.

Prior studies have identified a vast number of compositions that when added to isolated neurons in culture, appear to enhance, retard or repel cell growth. Growth promoters include complex reagents like serum, growth factors like NGF, specific guidance molecules like netrins and semaphorins, and many small molecule activators, like 7β-Acetoxy-8,13-epoxy-1α,6β,9α-trihydroxylabd-14-ene-11-one (U.S. Pat. No. 6,268,352; Song et al. 1998, Science 281, 1515–18). However, those skilled in the art recognize that in vitro growth regulation of isolated neurons is not predictive of the behavior of CNS neurons in an environment where they are subject to growth repulsion mediated by endogenous neural growth repulsion factors (see review by Tessier-Lavigne and Goodman (1996, Science 274, 1123–1133); compounds found to promote nerve growth in vitro and/or in embryonic systems are generally unable to overcome in situ repulsion present in the adult CNS.

It is well known that peripheral nerves enjoy a robust regenerative capacity whereas CNS nerves do not, which has been attributed to the presence of axon growth inhibitory molecules in CNS oligodendrocyte-derived myelin (1–3) including myelin associated glycoprotein (MAG). Immobilized CNS myelin proteins have been shown to potently inhibit axon outgrowth from a variety of neurons in vitro (4). Moreover, anti-myelin antibodies have been used to neutralize the inhibitory effects of myelin and, more importantly, stimulate regeneration of the corticospinal tract in vivo (5). Thus far three of the inhibitory components of CNS myelin have been identified—MAG (6, 7), NOGO-A (8–10) and chondroitin sulfate proteoglycan (CSPG) (11). A recent study using a Xenopus spinal neuron-based growth cone turning assay had implicated PI3K in mediating the repulsive effects of MAG (12), raising the question as to how such a general signaling molecule is involved in inhibiting axon regeneration.

In preliminary experiments reported below, we show that such inhibitory activities of myelin components involve three signaling pathways, namely mitogen activated protein kinase kinases (MEK), phosphoinositide 3-kinase (PI3K) and phospholipase C-g (PLC-g). Among these, we show that the activation of an important target of PI3K, the serine/threonine kinase Akt, promotes or inhibits neurite outgrowth in different types of neurons. Moreover, modulating the activity of protein kinase C is able to switch Akt-elicited responses between promotion and inhibition. Based on these findings, we undertook investigations on the ability of PKC inhibitors to promote clinically relevant spinal axon regeneration. We disclose that treatment with PKC inhibitors surprisingly and dramatically stimulates neurite outgrowth in the presence of CNS myelin both in vitro and in vivo. Our findings demonstrate that inhibiting the intracellular PKC activity provides an effective therapeutic avenue to promote axon regeneration after CNS injury.

SUMMARY OF THE INVENTION

The invention provides methods for promoting regenerative growth of an adult mammalian central nervous system neuron axon subject to growth inhibition by endogenous, myelin growth repulsion factors. The method generally comprises the steps of delivering to the axon a therapeutically effective amount of a specific inhibitor of protein kinase C, whereby regenerative growth of the axon is promoted; and detecting a resultant promotion of the regenerative growth of the axon. In a particular application, the axon is an adult human central nervous system spinal neuron axon in situ and damaged by a spinal injury and the delivering step is effected by locally administering to a human patient in need thereof at the axon a therapeutically effective amount of the inhibitor.

DESCRIPTION OF PARTICULAR EMBODIMENTS OF THE INVENTION

The following descriptions of particular embodiments and examples are offered by way of illustration and not by way of limitation. Unless contraindicated or noted otherwise, in these descriptions and throughout this specification, the terms "a" and "an" mean one or more, the term "or" means and/or and polynucleotide sequences are understood to encompass opposite strands as well as alternative backbones described herein.

The invention provides methods for promoting regenerative growth of an adult mammalian central nervous system neuron axon subject to growth inhibition by endogenous, myelin growth repulsion factors. This regenerative growth requires a mature axon to overcome endogenous (naturally present in situ) repulsive factors present in adult mammals. The adult mammalian CNS, including that of the functionally adult CNS of 7–9 day post natal rats (below), imposes endogenous repulsive factors not present in neonatal or embryonic mammals. The method generally comprises the steps of delivering to the axon a therapeutically effective amount of a specific inhibitor of protein kinase C, whereby regenerative growth of the axon is promoted; and detecting a resultant promotion of the regenerative growth of the axon. The axon will typically be retained in situ, though the method can be practiced with a reconstituted in vitro system wherein the recited axon and repulsive factors are isolated. In a particular application, the axon is an adult human central nervous system spinal neuron axon in situ and damaged by a spinal injury and the delivering step is effected by locally administering to a human patient in need thereof at the axon a therapeutically effective amount of the inhibitor.

In particular applications, the inhibitor effectively inhibits classical type PKC present in the target CNS tissue. A wide variety of suitable inhibitors may be employed, guided by art-recognized criteria such as efficacy, toxicity, stability, specificity, half-life, etc. In particular embodiments, the inhibitor is elected from competitive inhibitors for the PKC ATP-binding site, including staurosporine and its bisindolyl-maleimide derivitives, Ro-31-7549, Ro-31-8220, Ro-31-8425, Ro-32-0432 and Sangivamycin; drugs which interact with the PKC's regulatory domain by competing at the binding sites of diacylglycerol and phorbol esters, such as calphostin C, Safingol, D-erythro-Sphingosine; drugs which target the catalytic domain of PKC, such as chelerythrine chloride, and Melittin; drugs which inhibit PKC by covalently binding to PKC upon exposure to UV lights, such as dequalinium chloride; drugs which specifically inhibit Ca-dependent PKC such as Gö6976, Gö6983, Gö7874 and other homologs, polymyxin B sulfate; drugs comprising competitive peptides derived from PKC sequence; and other PKC inhibitors such as cardiotoxins, ellagic acid, HBDDE, 1-O-Hexadecyl-2-O-methyl-rac-glycerol, Hypercin, K-252, NGIC-J, Phloretin, piceatannol, Tamoxifen citrate. Particular inhibitors shown to be effective in our earliest studies include:

542 (+−)-1-(5-Isoquinolinesulfonyl)-2-methylpiperazine dihydrochloride [H-7]; IC50 =6.0 uM 543 1-(5-Isoquinolinesulfonyl)piperazine [C-1];IC50=6.0 uM 609 (+/−)-Palmitoylcarnitine chloride 621 10-[3-(1-Piperazinyl)propyl]-2-trifluoromethylphenothiazine dimaleate 632 (+/−)-Stearoylcarnitine chloride Alternative pharmacologically acceptable inhibitors effective in the disclosed methods are readily screened from the wide variety of PKC inhibitors known in the art (e.g Goekjian et al., 2001 Expert Opin Investig Drugs 10, 2117–40; Battaini, 2001, Pharmacolog Res 44, 353–61) using the disclosed in vivo protocols.

Detailed protocols for implementing the recited steps are exemplified below and/or otherwise known in the art as guided by the present disclosure. The recited delivering and detecting steps are tailored to the selected system. In vitro systems provide ready access to the recited mixture using routine laboratory methods, whereas in vivo systems, such as intact organisms or regions thereof, typically require surgical or pharmacological methods. More detailed such protocols are described below. Similarly, the detecting step is effected by evaluating any suitable metric of axon growth, such as evaluated by linear measure, density, host mobility or other function improvement, etc.

In particular applications, the target cells are injured mammalian neurons in situ, e.g. Schulz M K, et al., Exp Neurol. February 1998; 149(2): 390–397; Guest J D, et al., J Neurosci Res. 1997 Dec. 1; 50(5): 888–905; Schwab M E, et al., Spinal Cord. July 1997; 35(7): 469–473; Tatagiba M, et al., Neurosurg March 1997; 40(3): 541–546; and Examples, below. For these in situ applications, compositions comprising the recited inhibitor may be administered by any effective route compatible with therapeutic activity of the compositions and patient tolerance. For CNS administration, a variety of techniques is available for promoting transfer of therapeutic agents across the blood brain barrier including disruption by surgery or injection, drugs which transiently open adhesion contact between CNS vasculature endothelial cells, and compounds which facilitate translocation through such cells. The compositions may also be amenable to direct injection or infusion, intraocular administration, or within/on implants e.g. fibers such as collagen fibers, in osmotic pumps, grafts comprising appropriately transformed cells, etc.

In a particular embodiment, the inhibitor is delivered locally and its distribution is restricted. For example, a particular method of administration involves coating, embedding or derivatizing fibers, such as collagen fibers, protein polymers, etc. with therapeutic agents, see also Otto et al. (1989) J Neurosci Res. 22, 83–91 and Otto and Unsicker (1990) J Neurosc 10, 1912–1921. The amount of inhibitor administered depends on the agent, formulation, route of administration, etc. and is generally empirically determined and variations will necessarily occur depending on the target, the host, and the route of administration, etc.

The compositions may be advantageously used in conjunction with other neurogenic agents, neurotrophic factors, growth factors, anti-inflammatories, antibiotics etc.; and mixtures thereof, see e.g. Goodman & Gilman's The Pharmacological Basis of Therapeutics, 9$^{th}$ Ed., 1996, McGraw-Hill. As noted below, the inhibitor can convert a co-administered agent from growth repulsive to growth promotive. Exemplary such other therapeutic agents include neuroactive agents such as in Table 1.

TABLE 1

Neuroactive agents which may be used in conjunction with PKC inhibitors.

| | | |
|---|---|---|
| NGF | Heregulin | Laminin |
| NT3 | IL-3 | Vitronectin |
| BDNF | IL-6 | Thrombospondin |
| NT4/5 | IL-7 | Merosin |
| CNTF | Neuregulin | Tenascin |
| GDNF | EGF | Fibronectin |
| HGF | TGFa | F-spondin |
| bFGF | TGFb1 | Netrin-1 |
| LIF | TGFb2 | Netrin-2 |
| IGF-I | PDGF BB | Semaphorin-III |
| IGH-II | PDGF AA | L1-Fc |
| Neurturin | BMP2 | NCAM-Fc |
| Percephin | BMP7/OP1 | KAL-1 |

Abbreviations:
NGF, nerve growth factor;
NT, neurotrophin;
BDNF, brain-derived neurotrophic factor;
CNTF, ciliary neurotrophic factor;
GDNF, glial-derived neurotrophic factor;
HGF, hepatocyte growth factor;
FGF, fibroblast growth factor;
LIF, leukemia inhibitory factor;
IGF, insulin-like growth factor;
IL, interleukin;
EGF, epidermal growth factor;
TGF, transforming growth factor;
PDGF, platelet-derived growth factor;
BMP, bone morphogenic protein;
NCAM, neural cell adhesion molecule.

In particular embodiments, the inhibitor is administered in combination with a pharmaceutically acceptable excipient such as sterile saline or other medium, gelatin, an oil, etc. to form pharmaceutically acceptable compositions. The compositions and/or compounds may be administered alone or in combination with any convenient carrier, diluent, etc. and such administration may be provided in single or multiple dosages. Useful carriers include solid, semi-solid or liquid media including water and non-toxic organic solvents. As such the compositions, in pharmaceutically acceptable dosage units or in bulk, may be incorporated into a wide variety of containers, which may be appropriately labeled with a disclosed use application. Dosage units may be included in a variety of containers including capsules, pills, etc.

The invention also provides pharmaceutical screens for modulators of disclosed PKC inhibitor-mediated mammalian CNS neuron axon regenerative growth, particularly, methods for characterizing an agent as modulating such regenerative growth by practicing the disclosed methods in the presence of a candidate agent, whereby but for the presence of the agent, the axon provides a reference regeneration; measuring an agent-biased regenerative growth of the axon; and comparing the reference and agent-biased regenerative growth, wherein a difference between the reference and agent-biased regenerative growth indicates that the agent modulates PKC inhibitor-mediated regenerative growth promotion.

The invention also provides compositions and mixtures specifically tailored for practicing the subject methods, including implantable, injectable or otherwise deliverable fibers, pumps, stents, or other devices loaded with premeasured, discrete and contained amounts of PKC inhibitor and specifically suited, adapted and/or tailored for the recited CNS axon delivery. Kits for practicing the disclosed methods may also comprises printed or electronic instructions describing the applicable subject method.

EXAMPLES

Blocking Myelin Inhibition of Axon Regeneration by Attenuating PKC Activity In Vitro We examined whether MAG treatment would lead to the activation of Akt, a well-characterized PI3K effector (13), in NG-108 cells, a known MAG-responsive rat neuronal cell line (6). After treatment with soluble recombinant MAG (250 ng/ml) for 10 minutes, the cell lysates are blotted with phospho-specific antibodies against Akt. Since both mitogen activated protein kinase kinases (MEK) and phospholipase C-g (PLC-g) pathways have been implicated in mediating axonal responses induced by neurotrophins (12, 14), we also examined activation of these pathways by phospho-specific antibodies against Erk and PLC-g, respectively. We found that all three pathways were strongly activated by MAG. The Akt activation by MAG was further confirmed by using an Akt kinase assay. Therefore, MAG activates three major pathways that have been shown to play crucial roles in mediating neuronal responses to neurotrophins and other growth factors (15).

To assess the functional relevance of the activation of the PI3K, MEK and PLC-g pathways, we utilized a standard neurite outgrowth assay in which NG108 cells or cerebellar granule neurons (CGN) from postnatal day 7–9 (P7–9) rats were grown on immobilized recombinant MAG or myelin (5–10, 16). Pharmacological inhibitors of the individual pathways—LY294002 and wortmannin for PI3K, U0126 for MEK, and U73122 for PLC-g, were then added to assess whether and to what extent these inhibitors could overcome the inhibitory activity of MAG or of myelin. Both LY294002 (10 mM) and wortmannin (50 nM) triggered robust neurite outgrowth in CGNs and in NG 108 cells on a MAG substrate, indicating that the PI3K pathway is not only activated, but also required in MAG-elicited inhibition. U0126 also promoted neurite outgrowth on the MAG substrate. As MEK has been previously shown to be required for axon growth induced by chronic exposure to neurotrophins (14), but not for growth cone turning in acute responses to NGF gradients (12), our results of abolishing MAG inhibition by an MEK inhibitor imply that the MEK pathway can be required only for neurite outgrowth in response to external cues. Consistent with previous studies (12), the PLCg inhibitor U73122 appeared toxic to both NG108 cells and CGNs even at 100 nM, thus preventing a direct assessment of the contribution of PLCg to neurite outgrowth. The inhibitors of both PI3K and MEK pathways also significantly stimulated neurite outgrowth from neurons cultured on CNS myelin.

Having determined that the PI3K pathway is both activated and required in MAG signaling, we next examined whether Akt, a major downstream effector of PI3K in promoting cell survival (13, 17) and in determining the directionality of cell movement during chemotaxis (18), could account for the neurite inhibitory effect of MAG. To this end, we transfected NG108 cells with three versions of the Akt product—a constitutive active, a dominant negative and a wild type form (19), and compared their effects on neurite outgrowth. On MAG and CNS myelin substrates, expression of dominant negative, but not wild type or constitutively active Akt, prompted robust neurite outgrowth and often resulted in multiple processes per neuron. This indicated that Akt was an effector of PI3K in mediating the inhibitory activity of MAG and perhaps other myelin associated inhibitors. The effect on neurite outgrowth appears independent of Akt's role in cell survival, as expression of the various Akt forms did not significantly affect the viability of transfected NG-108 cells. In addition, although enhancing cell survival, addition of ZVAD (10 mM), an irreversible ICE-like proteinase inhibitor (20), did not affect the pro-growth effect of the dominant negative form of Akt. Consistently, a phosphatidylinositol ether analog that potently and specifically inhibits Akt (21), when included in the culture medium, promoted robust process outgrowth from NG108 cells on myelin substrates. Together, these results indicate that Akt activity is required for the outgrowth-inhibitory effects of MAG and perhaps some of the other myelin components. On the other hand, overexpression of a constitutively active form of Akt prevented neurite outgrowth from NG108 cells on both poly-D-lysine (PDL) and myelin substrates, indicating that activation of Akt is sufficient to inhibit neurite outgrowth in these cells.

Since Akt has been thought of as a positive regulator of neurite outgrowth (21), our results with over-expression of constitutively active Akt came as a surprise. To resolve this, we transfected the active form of Akt into rat P7 CGNs and found that the majority of transfected neurons had longer processes than those of wild type Akt-transfected neurons on a PDL substrate. However, expression of dominant negative Akt led to the death of the transfected CGNs, consistent with a critical role of Akt in promoting cell survival (13, 17 and 19). Thus, the neurite outgrowth response elicited by Akt activation differs in a cell type specific manner.

Growth cone responses can be converted from attraction to repulsion and vice versa through the modification of cellular cyclic nucleotide levels (12, 16, 23). The opposing effects of Akt activation on neurite outgrowth suggest that this pathway may be subjected to regulation by other coincidently occurring signaling activities. Agents that modulate cAMP or cGMP levels did not significantly affect the neurite outgrowth responses elicited by overexpressing different forms of Akt in NG108 cells, implying the existence of alternative modulatory mechanisms. As the PLCg pathway is activated by MAG and PKC is a major effector of PLCg (15), we assessed whether changes in PKC activity could affect the activity of different forms of Akt in NG-108 cells on the PDL substrate. To our surprise, the majority of constitutively active Akt expressing NG108 cells extended processes following treatment with 5 mM bisindolylmaleimide (GFX, a PKC inhibitor), while exposure to 100 nM phorbol myristate-13-acetate (PMA), a PKC activator, resulted in inhibition of neurite outgrowth from cells expressing the dominant negative version of Akt. Similarly, PMA also abolished the neurite outgrowth promoting activity of active Akt in CGNs. As both GFX and PMA treatments did not result in significant alterations in neurite outgrowth from untransfected cells and those transfected with wild type Akt, we conclude that PKC acts by modulating components in the Akt-elicited signaling pathway.

Based on the modulation of neurite outgrowth by modulating PKC activity, we predicted that inhibiting PKC activity might abolish or convert the inhibitory responses of neurons to MAG and other myelin-associated inhibitors. Our data show that neurite outgrowth from both P7–9 rat CGNs and dorsal root ganglion (DRG) sensory neurons was inhibited by immobilized CNS myelin. Addition of sp-cAMP stimulated neurite outgrowth, consistent with previous reports that activation of PKA allows neurons to overcome inhibition by MAG and perhaps other inhibitors in CNS myelin (16). The switching effects of sp-cAMP on the neurite outgrowth responses elicited by CNS myelin, but not by Akt overexpression, suggested that PKA exerted its effect in an Akt-independent manner. As expected, several PKC inhibitors, including GFX, Gö6976, and calphostin, profoundly affected neurite outgrowth by enhancing both the number of neurite-bearing cells and the length of neurites in both CGN and DRG neurons. Based on existing evidence for the functional interactions between the PKA and PKC pathways (24), we conclude that both PKA and PKC act through parallel mechanisms in affecting neurite outgrowth. Although many PKC isoforms are expressed in the nervous system (25), our observations with phorbol ester and selective PKC inhibitors indicate the involvement of at least classical PKC isoforms whose activation is dependent on diacylglycerol (DAG) and calcium (24).

Our findings indicate that Akt is a key signaling molecule in mediating the inhibitory activity of MAG and perhaps other myelin associated inhibitors and that intracellular PKC activity participates in setting the cytoskeletal responses to Akt-mediated signaling pathways in neuronal cells. Also implicit in our study is a general mechanism whereby combinatorial activation of multiple signaling pathways can determine the action specificity of different environmental cues. As many physiological signals affect neuronal PKC activity (24), our results unravel a novel means by which neuronal responses to environmental cues are fine-tuned, in addition to the documented effects of modulating cyclic nucleotide levels (12, 16, 23).

Blocking Myelin Inhibition of Axon Regeneration by Attenuating PKC Activity In Vivo Our results from the in vitro studies prompted us to examine whether inhibition of PKC activity could stimulate neurite outgrowth in CNS white matter in vivo. We thus injected vehicle or Gö6976-treated P7 rat CGNs into the ventral funiculus of the adult rat spinal cord and examined neurite outgrowth of these transplanted neurons within the white matter that is largely composed of myelinated axons (26). Two weeks after transplantation, both groups of cells had similar survival rates. However, less than 3% of the vehicle-treated CGNs elaborated neurites and none of the outgrowing neurites attained lengths equivalent to their soma diameters. In striking contrast, Gö6976-treated neurons showed robust neurite outgrowth in which 85% of the donor neurons bore neurites and 80% of these neurons had neurites longer than twice their soma diameters. Confocal analysis confirmed that extended neurites were derived from transplanted CGNs. In subsequent experiments, similar in vivo efficacy is demonstrated with a panel of alternative exemplary PKC inhibitors (Table 2, below).

Corticospinal Tract (CST) Regeneration Assay. PKC inhibitors are assayed for their ability to improve corticospinal tract (CST) regeneration following thoracic spinal cord injury by promoting CST regeneration into human Schwann cell grafts in the methods of Guest et al. (1997, supra). For these data, the human grafts are placed to span a midthoracic spinal cord transection in the adult nude rat, a xenograft tolerant strain. Inhibitors are incorporated into a fibrin glue and placed in the same region. Anterograde tracing from the motor cortex using the dextran amine tracers, Fluororuby (FR) and biotinylated dextran amine (BDA), are performed. Thirty-five days after grafting, the CST response is evaluated qualitatively by looking for regenerated CST fibers in or beyond grafts and quantitatively by constructing camera lucida composites to determine the sprouting index (SI), the position of the maximum termination density (MTD) rostral to the GFAP-defined host/graft interface, and the longitudinal spread (LS) of bulbous end terminals. The latter two measures provide information about axonal die-back. In control animals (graft only), the CST do not enter the SC graft and undergo axonal die-back. As shown in Table 2, the exemplified inhibitors dramatically reduce axonal die-back and cause sprouting.

TABLE 2

In Vivo Neuronal Regeneration with Exemplary PKC Inhibitors.

| PKC Inhibitor | Reduced Die-Back | Promote Sprouting |
| --- | --- | --- |
| 1. staurosporine | +++ | ++++ |
| 2. Ro-31-7549 | ++++ | ++++ |
| 3. Ro-31-8220 | ++++ | +++ |
| 4. Ro-31-8425 | +++ | ++++ |
| 5. Ro-32-0432 | ++++ | ++++ |
| 6. Sangivamycin | ++++ | ++++ |
| 7. calphostin C | +++ | +++ |
| 8. Safingol | ++++ | ++++ |
| 9. D-erythro-Sphingosine | ++++ | +++ |
| 10. chelerythrine chloride | +++ | ++++ |
| 11. Melittin | ++++ | ++++ |
| 12. dequalinium chloride | ++++ | ++++ |
| 13. Gö6976 | ++++ | +++ |
| 14. Gö6983 | +++ | +++ |
| 15. Gö7874 | ++++ | ++++ |
| 16. cpPKC5858 (competitive PKC peptide) | ++++ | +++ |
| 17. cpPKC3487 (competitive PKC peptide) | ++++ | ++++ |
| 18. cpPKC3109 (competitive PKC peptide) | +++ | ++++ |
| 19. cardiotoxin | ++++ | +++ |
| 20. ellagic acid | +++ | +++ |
| 21. HBDDE | ++++ | ++++ |
| 22. 1-O-Hexadecyl-2-O-methyl-rac-glycerol | +++ | +++ |
| 23. Hypercin | +++ | +++ |
| 24. K-252 | ++++ | ++++ |
| 25. NGIC-I | ++++ | ++++ |
| 26. Phloretin | +++ | +++ |
| 27. piceatannol | ++++ | ++++ |
| 28. Tamoxifen citrate. | ++++ | +++ |

Peripheral Nerve Regeneration Assay. The PKC inhibitors of Table 2 are also incorporated in the implantable devices described in U.S. Pat. No. 5,656,605 and tested for the promotion of in vivo regeneration of peripheral nerves. Prior to surgery, 18 mm surgical-grade silicon rubber tubes (I.D. 1.5 mm) are prepared with or without guiding filaments (four 10-0 monofilament nylon) and filled with test compositions comprising the inhibitors of Table 2. Experimental groups consist of: 1. Guiding tubes plus Biomatrix 1™ (Biomedical Technologies, Inc., Stoughton, Mass.); 2. Guiding tubes plus Biomatrix plus filaments; 3–23. Guiding tubes plus Biomatrix 1 plus inhibitors.

The sciatic nerves of rats are sharply transected at mid-thigh and guide tubes containing the test substances with and without guiding filaments sutured over distances of approximately 2 mm to the end of the nerves. In each experiment, the other end of the guide tube is left open. This model simulates a severe nerve injury in which no contact with the distal end of the nerve is present. After four weeks, the distance of regeneration of axons within the guide tube is tested in the surviving animals using a functional pinch test. In this test, the guide tube is pinched with fine forceps to mechanically stimulate sensory axons. Testing is initiated at the distal end of the guide tube and advanced proximally until muscular contractions are noted in the lightly anesthetized animal. The distance from the proximal nerve transection point is the parameter measured. For histological analysis, the guide tube containing the regenerated nerve is preserved with a fixative. Cross sections are prepared at a point approximately 7 mm from the transection site. The diameter of the regenerated nerve and the number of myelinated axons observable at this point are used as parameters for comparison.

Measurements of the distance of nerve regeneration document therapeutic efficacy. Similarly, plots of the diameter of the regenerated nerve measured at a distance of 7 mm into the guide tube as a function of the presence or absence of one or more inhibitors demonstrate a similar therapeutic effect of all 28 tested. No detectable nerve growth is measured at the point sampled in the guide tube with the matrix-forming material alone. The presence of guiding filaments plus the matrix-forming material (no agents) induces only very minimal regeneration at the 7 mm measurement point, whereas dramatic results, as assessed by the diameter of the regenerating nerve, are produced by the device which consisted of the guide tube, guiding filaments and inhibitor compositions. Finally, treatments using guide tubes comprising either a matrix-forming material alone, or a matrix-forming material in the presence of guiding filaments, result in no measured growth of myelinated axons. In contrast, treatments using a device comprising guide tubes, guiding filaments, and matrix containing inhibitor compositions consistently result in axon regeneration, with the measured number of axons being increased markedly by the presence of guiding filaments.

In Situ Promotion of Functional Recovery and Neurite Outgrowth

PKC inhibitors are assayed for their ability to improve functional recovery and neurite outgrowth following traumatic cord injury, essentially as described by White, 1998, Neurosci 86, 257–63. To examine whether PKC inhibitors induce hyperalgesia and changes in the area of termination of myelinated sensory neurons in the spinal cord, we continuously administer our exemplary inhibitors (Table 2) intrathecally (into spinal subarachnoid space) for two weeks in normal and traumatized rats (350 g). For this, 8 cm of PE 10 tubing is inserted through the cisterna magna in anaesthetized animals (Yaksh et al., 1976, Physiol Behav 17, 1031–36). Rats with and without trauma-induced neurological deficits are used for behavioral and transganglionic labeling studies.

The nociceptive flexion reflex is quantified with an Ugo Basile Analgesymeter (Comerio-Varese, Italy). This device generates a mechanical force that increases linearly with time. The force is applied to the dorsum of the rat's hindpaw, by a cone-shaped plunger (diameter 1.4 mm, radius of curvature 36°). The nociceptive threshold is defined as the force, in grams, at which the rat withdraws its paw. Nociceptive thresholds are determined on a daily basis, five days before and two weeks after the commencement of intrathecal administration of inhibitor (n=5) or saline (n=4), at 10-min intervals for a period of 2 h. The mean of the last six measurements represents the nociceptive threshold for that day. After measuring thresholds on the fifth day, animals are re-anaesthetized and osmotic pumps (0.5 ul/h; 14 days; Alzet, Calif.) were attached to the PE tubing and implanted subcutaneously. All solutions delivered by osmotic pumps contained 10 U/ml heparin and saline served as the vehicle control.

On the completion of the behavioral studies, animals treated intrathecally with inhibitor or saline are used for transganglionic labeling to examine the area of termination of myelinated A-fibers in the spinal cord. For this, rats are re-anaesthetized, the sciatic nerve exposed, and 2 ul of a 0.5% solution of C-HRP (dissolved in saline; List Biological Laboratories, Campbell, Calif.), which labels myelinated fibers (LaMotte et al., 1991, J Comp Neurol 311, 546–62), injected into the nerve via a Hamilton syringe with a 33-gauge needle. The wound is closed and the rats allowed to recover. After two to three days, the rats are overdosed with sodium pentobarbitone and perfused via the left ventricle with 250 ml of 0.1 M phosphate-buffered saline followed by 1000 ml of 4% paraformaldehyde in 0.1 M phosphate buffer (pH 7.4) over 1 h, then by 500 ml of 30% sucrose in phosphate-buffered saline. The lumbar spinal cord is removed and stored overnight in 30% sucrose. 50 ul sections are cut on a freezing microtome. Sections are reacted for horseradish peroxidase using tetramethylbenzidine as the chromogen, dehydrated, cleared and mounted, and the pattern of terminal labeling across the different laminae determined.

We find that intrathecal administration of the PKC inhibitors of Table 2 into both normal and traumatized rats induces a significant decrease in threshold to mechanical stimulation in the paw withdrawal test compared to saline-treated control animals. Transganglionic labeling of primary afferent neurons of the sciatic nerve with C-HRP following intrathecal saline results in C-HRP label transported to laminae I, III and deeper laminae of the lumbar spinal cord.

PKC Mediates Inhibitory Effects of CNS Myelin and Chondroitin Sulfate Proteoglycans (CSPGs) on Axonal Regeneration Screening for compounds that allow neurite outgrowth from postnatal day 7–9 rat cerebellar granule neurons (CGNs) on CNS myelin substrates, we identified several broad-specificity PKC inhibitors from a small molecule libraries. Based on their structure and substrate requirements, PKC isoforms can be divided into three classes: the Ca++ and second messenger diacylglycerol (DAG)-sensitive conventional PKCs (-α, -β, and -γ), the Ca++-independent but DAG-dependent novel PKCs (-δ, -ε, -η, -θ, and -μ), and the Ca++- and DAG-insensitive atypical PKCs (-ζ and -λ). We first examined PKC inhibitors with a higher specificity for the conventional class of PKC isotypes for their ability to promote neurite outgrowth on CNS myelin. These inhibitors included Chelerythrine, Calphostin, Bisindoleylmaleimide I, and Gö6976. Dose response experiments (in the range of 10 nM to 10 uM) were carried out for each PKC inhibitor. At 100 nM, treatment with Gö6976 and Calphostin C profoundly mitigated outgrowth inhibition and promoted significant neurite outgrowth on a CNS myelin substrate. Quantification analysis indicated that the effects of these PKC inhibitors were comparable to that of Y-27632, an inhibitor of Rho associated kinase, which has been previously shown to block the inhibitory activity of CNS myelin and its components. However, Rp-8-Br-cGMPS, an inhibitor of protein kinase G (PKG), failed to overcome the inhibitory effects of CNS myelin. Further, Gö6976 and Calphostin C efficiently overcame neurite outgrowth inhibition induced by the three individual myelin inhibitors, i.e. MAG, Nogo-A and OMgp, indicating that these components can account for the majority of myelin-associated inhibitory activities.

Consistent with a functional involvement of conventional PKC isoforms in mediating the inhibitory activity of myelin components, Western blotting analysis revealed that both PKC-α, and-β are highly expressed in cultured CGNs, even though these neurons also express members of novel and atypical PKCs. We exploited the fact that specific kinase mutant forms of PKC that retain all of their activity except for binding ATP can act to inhibit the activity of the corresponding endogenous PKC isotypes in a dominant negative manner. Thus, we made recombinant retroviruses to express both wild-type and dominant negative forms of conventional, atypical and novel isoform PKCs and expressed these proteins in P4 CGNs for neurite outgrowth assays using CNS myelin as the substrate. The expression levels of these exogenous proteins were comparable as detected by Western blotting. Although expression of individual proteins did not affect neurite outgrowth from cultured neurons on poly-D-lysine (PDL) substrate, mutant, but not wild type PKC-α, and-β prompted robust neurite outgrowth from the neurons on myelin substrate. Collectively, these pharmacological and genetic data indicate that members of the conventional PKC subclass are involved in the restrictive activity of myelin associated inhibitors.

We examined whether PKC is involved in the inhibitory activity of CSPG, the other major inhibitory activity associated with glial scars in the adult CNS. Consistent with previous studies, Y-27632 allowed the cultured neurons to overcome the inhibitory activity of CSPG. Similarly, the presence of conventional PKC inhibitors, but not LY294002, an inhibitor of PI-3 kinase, also resulted in robust neurite outgrowth from neurons on CSPG substrate. Consistently, we also found that expression of mutant, but not wild type PKC-α, and-β also allowed extensive neurite outgrowth, indicating that PKC participated in the inhibitory pathways of both myelin components and CSPG. Both PKC inhibitors and the ROCK inhibitor Y-27632 showed stronger effects than chondroitinase ABC.

We also assessed whether individual inhibitors affect endogenous PKC activity in treated neurons. After stimulation of the CGNs with soluble MAG-Fc (10 nM), AP-Nogo-66 (20 nM) or CSPG (50 ng/ml), conventional PKC activity was found to be elevated as determined by blotting the resultant lysates with anti-phospho-PAN PKC antibodies. However, the same treatments did not result in the activation of atypical and novel PKC isoforms as detected by corresponding specific phospho-antibodies. To further confirm the role of PKC as a direct signaling mediator, we examined whether PKC activation by myelin inhibitors is dependent on NgR, a required receptor component for all of the three major myelin inhibitors. Thus, we used recombinant retroviruses to overexpress full-length or dominant negative NgR in CGNs and examined PKC activation in these transduced neurons by NgR ligands. MAG-elicited PKC activation was markedly reduced in neurons overexpressing dominant negative, but not full length NgR. An additional and critical signaling event shared by these inhibitory activities is the activation of the small GTPase RhoA. In order to determine the relationship between PKC and RhoA in these pathways, we stimulated cultured CGNs with MAG-Fc, AP-Nogo-66 or CSPG in the presence or absence of Gö6976 and examined the RhoA activation in these conditions by subjecting the resulting cell lysates to a RhoA pull down assay. We found that Gö6976 blocked MAG-Fc, AP-Nogo-66 and CSPG induced RhoA activation in a dose dependent manner. Thus, conventional PKCs participate in transducing the inhibitory signals of both myelin inhibitors and CSPG from their specific cell surface receptors to activate RhoA.

Intrathecal Infusion of Gö6976 Promotes Dorsal Column Axonal Regeneration Following Upper Cervical Spinal Dorsal Hemisection To assess the contribution of PKC mediated inhibitory effects on axon regeneration in vivo, we examined whether intrathecal infusion of Gö6976 affected regeneration of dorsal column ascending axons following spinal cord dorsal hemisection in adult rats. The hemisection was performed between the 3rd and 4th cervical spinal segments (C3–4) to a depth of 1.6 mm from the dorsal surface of the cord using a VibraKnife device that can be used to precisely control the lesion depth stereotaxically. To ensure that bilateral dorsal columns were completely transected, the lesion was advanced ventrally to the level of central cannel resulting in the transection of the entire dorsal half of the spinal cord. After the lesion, dura mater was sutured to restore cerebespinal fluid circulation and to prevent connective tissue invasion. Intrathecal delivery of Gö6976 (20 uM) or saline vesicle into the lesion site was achieved by constant infusion of the compound at a rate of 0.5 ul/hr for 14 days using an Alzet mini-osmotic pump (Model 2002). Five weeks after surgery, a narrow lesion gap through the dorsal half of the cord was clearly seen, confirming the completeness of dorsal column transection. Unlike conventional lesioning methods that usually cause secondary tissue damage and cavitation, the VibraKnife lesioning resulted in well-preserved cord stumps with few cavities. Anatomical regeneration of injured dorsal column axons was assessed by anterograde tracing of Cholera toxin B subunit (CTB) which was injected into bilateral sciatic nerves and brachial plexuses.

In all rats that received Gö6976 infusion, CTB-labeled axons were seen to cross the lesion gap and grow within the distal host spinal cord for a considerable distance. Neurolucida reconstruction from a single section of Gö6976-treated case showed the presence of CTB-labeled regenerated axons through and beyond the lesion although relatively fewer fibers were found within the lesion gap, which could be an effect of gliotic response to axons traversing through the lesion. The presence of numerous neurofilament-(NF) positive axons within the lesion gap in cases that received G ö6976 treatment implies that many of these NF-positive axons were regenerating dorsal column axons that might have not been recognized by the CTB-antibody due to the gliotic response. Strikingly, after crossing the lesion gap, regenerating dorsal column axons grew back into their original pathway, the dorsal column, and elongated along their tracts for a considerable distance. In fact, many regenerated axons ended at 7 mm distal to the injury, the longest distance that was examined. Notably, CTB-labeled axons not only regenerated within the distal dorsal column but also branched into the adjacent gray matter, as did their proximal counterparts. In contrast to the remarkable axonal regeneration observed in the Gö6976-treatment group, infusion of vehicle into the lesion gap did not promote axonal regeneration across the lesion gap. These results together demonstrate that the dorsal column axonal regeneration beyond the injury can be attributed to the effect of infused Gö6976. In subsequent studies, we similarly show that regenerating axons after Gö6976 treatment are able to establish functional connections with neurons in the dorsal column nuclei, which in turn improves physiological and behavioral recovery.

Cited References

1. M. E. Schwab, D. Bartholdi. *Physiol. Rev.* 76, 319–370 (1996).
2. P. J. Homer, F. H. Gage. *Nature* 407, 963–970 (2000).
3. M. E. Schwab. *Science* 295, 1029–1031 (2002).
4. P. Caroni, M. E. Schwab. *Neuron* 1, 85–96 (1988).
5. D. W. Huang, L. McKerracher, P. E. Braun, S. David. *Neuron* 24, 639–647 (1999).
6. L. McKerracher, L et al., *Neuron* 13, 805∝811 (1994).
7. G. Mukhopadhyay, et al., *Neuron* 13, 757–767 (1994).
8. M. S. Chen, et al., *Nature* 403, 434–439 (2000).
9. T. GrandPre, F. Nakamura, T. Vartanian, S. M. Strittmatter. *Nature* 403, 439–444 (2000).
10. Prinjha, R. et al., *Nature* 403, 383–384 (2000).
11. B. P. Niederost, et al. *J Neurosci* 19, 8979–8989 (1999).
12. G. Ming, et al. *Neuron* 23, 139–148 (1999).
13. D. A. Fruman, R. E. Meyers, L. C. Cantley. *Annu Rev Biochem* 67, 481–507 (1998).
14. J. K. Atwal, B. Massie, F. D. Miller, D. R. Kaplan. *Neuron* 27, 265–277 (2000).
15. R. A. Segal, M. E. Greenberg. *Annu Rev Neurosci* 19, 463–489 (1996).
16. D. Cai, Y. Shen, M., De Bellard, S. Tang, M. T. Filbin. *Neuron* 22, 89–101(1999).
17. S. R. Datta, A. Brunet, M. E. Greenberg. *Genes Dev* 13, 2905–2927 (1999).
18. C. Y. Chung, S. Funamoto, R. A. Firtel. *Trends Biochem Sci* 26, 557–566 (2001).
19. A. Brunet, A. Bonni, M. J. Zigmond, M. Z. Lin, P. Juo, et al., *Cell* 96, 857–868 (1999).
20. D. F. Chen, G. E. Schneider, J.-C. Martinou, S. Tonegawa. *Nature* 385, 434–439 (1997).
21. Y. Hu, et al. *J Med Chem* 43, 3045–3051 (2000).
22. K. Namikawa, et al. *J Neurosci* 20, 2875–2886 (2000).
23. H. Song, et al. *Science* 281, 1515–1518 (1998).
24. A. C. Newton. *Curr Opin Cell Biol* 9, 161–167 (1997).
25. E. M. Powell, Mercado M. L. T., Calle-Patino, Y., Geller H. M. *Glia* 33, 288–297 (2001).
26. Intra white matter transplantation of CGNs. P7 CGN (50,000 cells/ml) were prelabeled with Cell Tracker CM-DiI (1 mM; Molecular Probes, Eugene, Oreg.), pretreated with PBS or 50 nM Gö6976, and microinjected at the level of T9 into the spinal cord ventral funiculus of adult Sprague-Dawley rats (1 ml/per injection; N=3 for each group). Two pieces of 2 mm³ gelfoam (Pharmacia & Upjohn, Kalamazoo, Mich.) soaked with PBS or 500 nM Gö6976 were placed onto the spinal dura where the penetration for cell injection occurred. Spinal cords (8 mm in length centered around the CGN injection site) were collected 2 weeks after surgery, and 20 mm cryostat sagittal sections were made. DiI positive CGNs were examined with a fluorescent microscope (Omega XF-32 optical filter) in all sections of each cord to evaluate cell survival (27). Percentages of the neurite-bearing CGNs and CGNs with neurites longer than twice the soma length were quantified among 400 CGNs from a single 20 mm section of each cord that had the highest number of neurite-bearing CGNs.
27. Y. D. Teng, I. Mocchetti, J. R. Wrathall. *Eur J Neurosci* 10, 798–802 (1998)
28. T. Laux, et al. *J Cell Biol* 149, 1455–1472 (2000).
29. M. Lehmann, et al., *J Neurosci* 19, 7537–7547 (1999).
30. W. T. Norton, S. E. Poduslo. *J. Neurochem.* 21, 749–757 (1973).

The foregoing descriptions of particular embodiments and examples are offered by way of illustration and not by way of limitation. All publications and patent applications cited in this specification and all references cited therein are herein incorporated by reference as if each individual publication or patent application or reference were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for promoting regenerative growth of an adult human central nervous system neuron axon in situ and damaged by an injury and subject to growth inhibition by endogenous, myelin growth repulsion factors, the method comprising the steps of delivering to the axon a therapeutically effective amount of a specific inhibitor of a protein kinase C by locally administering to a human patient in need thereof at the axon said therapeuticaliy effective amount of the inhibitor, whereby regenerative growth of the axon is promoted; and detecting a resultant promotion of the regenerative growth of the axon, wherein the inhibitor is selected from the group consisting of: Ro-31-7549, Ro-31-8220, Ro-31-8425 and Ro-32-0432.

2. The method of claim 1, wherein the inhibitor is Ro-31-7549.

3. The method of claim 1, wherein the inhibitor is Ro-31-8220.

4. The method of claim 1, wherein the inhibitor is Ro-31-8425.

5. The method of claim 1, wherein the inhibitor is Ro-32-0432.

6. A method for promoting regenerative growth of an adult human central nervous system neuron axon in situ and damaged by an injury and subject to growth inhibition by endogenous, myelin growth repulsion factors, the method comprising the steps of delivering to the axon a therapeutically effective amount of a specific inhibitor of a Ca-dependent protein kinase C by locally administering to a human patient in need thereof at the axon said therapeutically effective amount of the inhibitor, whereby regenerative growth of the axon is promoted; and detecting a resultant promotion of the regenerative growth of the axon, wherein the inhibitor is selected from the group consisting of: Gö6976, Gö6983 and Gö7874.

7. The method of claim 6, wherein the inhibitor is Gö6976.

8. The method of claim 6, wherein the inhibitor is Gö6983.

9. The method of claim 6, wherein the inhibitor is Gö7874.

10. A method for promoting regenerative growth of an adult human central nervous system spinal neuron axon in situ and damaged by a spinal injury and subject to growth inhibition by endogenous, myelin growth repulsion factors, the method comprising the steps of delivering to the axon a therapeutically effective amount of a specific inhibitor of a Ca-dependent protein kinase C by locally administering to a human patient in need thereof at the axon said therapeutically effective amount of the inhibitor, whereby regenerative growth of the axon is promoted; and detecting a resultant promotion of the regenerative growth of the axon, wherein the inhibitor is selected from the group consisting of: (+−)-1-(5-Isoquinolinesulfonyl)-2-methylpiperazine dihydrochloride; 1-(5-Isoquinolinesulfonyl)piperazine; (+/−)-Palmitoylcarnitine chloride; 10-[3-(1-Piperazinyl)propyl]-2-trifluoromethylphenothiazine dimaleate, and (+/−)-Stearoylcamitine chloride.

11. The method of claim 10, wherein the inhibitor is (+/−)-1-(5-Isoquinolinesulfonyl)-2-methylpiperazine dihydrochloride.

12. The method of claim 10, wherein the inhibitor is 1-(5-Isoquinolinesulfonyl) piperazine.

13. The method of claim 10, wherein the inhibitor is (+/−)-Palmitoylcarnitine chloride.

14. The method of claim 10, wherein the inhibitor is 10-[3-(1-Piperazinyl)propyl]-2-trifluoromethylphenothiazine dimaleate.

15. The method of claim 10, wherein the inhibitor is (+/−)-Stearoylcarnitine chloride.

16. A method for promoting regenerative growth of an adult human central nervous system neuron axon in situ and damaged by an injury and subject to growth inhibition by endogenous, myelin growth repulsion factors, the method comprising the steps of delivering to the axon a therapeutically effective amount of a specific inhibitor of a Ca-dependent protein kinase C by locally administering to a human patient in need thereof at the axon said therapeutically effective amount of the inhibitor, whereby regenerative growth of the axon is promoted; and detecting a resultant promotion of the regenerative growth of the axon, wherein the inhibitor is selected fron the group consisting of: (+/−)-1-(5-Isoquinolinesulfonyl)-2-methylpiperazine dihydrochloride; 1-(5-Isoquinolinesulfonyl)piperazine; (+/−)-Palmitoylcarnitine chloride; 10-[3-(1-Piperazinyl)propyl]-2-trifluoromethylphenothiazine dimaleate; and (+/−)-Stearoylcarnitine chloride.

17. The method of claim 16, wherein the inhibitor is (+/−)-1-(5-Isoquinolinesulfonyl) -2-methylpiperazine dihydrochloride.

18. The method of claim 16, wherein the inhibitor is 1-(5-Isoquinolinesulfonyl)piperazine.

19. The method of claim 16, wherein the inhibitor is (+/−)-Palmitoylcarnitine chloride.

20. The method of claim 16, wherein the inhibitor is 10-[3-(1-Piperazinyl)propyl]-2-trifluoromethylphenothiazine dimaleate.

21. The method of claim 16, wherein the inhibitor is (+/−)-Stearoylcarnitine chloride.

* * * * *